(12) United States Patent
Erickson et al.

(10) Patent No.: US 8,827,927 B2
(45) Date of Patent: Sep. 9, 2014

(54) HUB FOR LOOP TIP DEVICES

(75) Inventors: Leonard Erickson, Lewisville, NC (US); Eric R. Hennessy, Lewisville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 700 days.

(21) Appl. No.: 13/078,358

(22) Filed: Apr. 1, 2011

(65) Prior Publication Data

US 2011/0245809 A1  Oct. 6, 2011

Related U.S. Application Data

(60) Provisional application No. 61/320,856, filed on Apr. 5, 2010.

(51) Int. Cl.
*A61B 5/00* (2006.01)

(52) U.S. Cl.
USPC ........................................................... 600/585

(58) Field of Classification Search
USPC ................ 600/585; 604/130, 164.13, 264, 604/533–536
See application file for complete search history.

(56) References Cited

U.S. PATENT DOCUMENTS

| | | | |
|---|---|---|---|
| 5,380,301 A | 1/1995 | Prichard et al. | |
| 6,569,151 B1 * | 5/2003 | Nash et al. | 604/533 |
| 7,144,378 B2 * | 12/2006 | Arnott | 600/585 |
| 7,328,071 B1 * | 2/2008 | Stehr et al. | 607/131 |
| 7,455,660 B2 * | 11/2008 | Schweikert et al. | 604/171 |
| 7,601,147 B2 | 10/2009 | Waller et al. | |
| 7,666,170 B2 * | 2/2010 | Guala | 604/249 |
| 7,717,865 B2 * | 5/2010 | Boutillette et al. | 600/585 |
| 8,025,629 B2 * | 9/2011 | Shelton | 600/585 |
| 8,038,628 B2 * | 10/2011 | Von Malmborg et al. | 600/585 |
| 8,454,536 B2 * | 6/2013 | Raulerson et al. | 600/585 |
| 8,585,651 B2 * | 11/2013 | Asai | 604/164.13 |
| 2003/0225397 A1 | 12/2003 | Baechtold | |
| 2005/0245847 A1 | 11/2005 | Schaeffer | |
| 2006/0015086 A1 | 1/2006 | Rasmussen et al. | |
| 2007/0043324 A1 | 2/2007 | Shibata et al. | |
| 2008/0147012 A1 | 6/2008 | Rome | |
| 2010/0022951 A1 | 1/2010 | Ferrera et al. | |

FOREIGN PATENT DOCUMENTS

WO   WO 2008/147957 A1   12/2008

OTHER PUBLICATIONS

International Search Report mailed Jul. 19, 2011 for International Application No. PCT/US2011/030864.
Written Opinion mailed Jul. 19, 2011 for International Application No. PCT/US2011/030864.

* cited by examiner

*Primary Examiner* — Max Hindenburg
(74) *Attorney, Agent, or Firm* — Brinks Gilson & Lione

(57) ABSTRACT

A hub device and a method for reception of a flexible elongate device therethrough are provided. The hub device includes a proximal portion having a substantially cylindrical opening defined in the proximal portion, a first connector at a proximal end of the proximal portion for connecting to a medical device and a distal portion connectable to an elongate shaft. The hub device further includes a lumen extending from the cylindrical opening in the proximal portion to a non-cylindrical cross-sectional lumen portion in the distal portion of the hub device, the lumen including a distal tapered portion tapering to the non-cylindrical cross sectional lumen portion. The distal tapered portion includes a first pair of longitudinal loop guides positioned on opposite sides of the lumen and configured to receive and collapse a loop of an elongate device received and distally advanced through the lumen.

11 Claims, 6 Drawing Sheets

HUB FOR LOOP TIP DEVICES

RELATED APPLICATIONS

This application claims the benefit of U.S. Provisional Application No. 61/320,856, filed Apr. 5, 2010, which is incorporated by reference herein in its entirety.

BACKGROUND

1. Technical Field

This invention relates to hubs for reception of wire guides used in the placement of medical devices, and more particularly to hubs for reception of wire guides having a loop tip.

2. Background Information

Wire guides are elongate flexible members used to provide a path along which another medical device can be moved. The path provided by the wire guide can be used to navigate another medical device, such as a catheter through a body vessel. The wire guide provides an established path for placing other devices and eliminates the need for performing delicate navigation procedures for each device passed into the body lumen, for example when additional procedures are performed.

During placement of the wire guide, an operator must navigate the wire guide through a tortuous pathway in the body lumen due to the presence of natural bends and/or curves, or unnatural impediments, such as tumors, build-ups, and/or strictures. The operator may chose to navigate the lumen with a standard wire guide having a generally straight distal tip or a loop tip wire guide having a deformable loop at the distal tip. Loop tip wire guides are beneficial in navigating tortuous pathways to avoid having the end of the wire guide trapped in a pocket or sharp curve. The loop tip flexes against the pathway to move the wire guide distally to the treatment site.

Several types of catheters, including treatment devices, are used in endoscopic procedures that are delivered to the treatment site over the wire guide. These catheters typically include a hub connected the proximal end of the catheter through which the wire guide is inserted and extended out of the distal end of the catheter for navigation of the wire guide through the pathway. Conventional hubs typically include a luer connector at a proximal end of the hub and are connected to the catheter at a distal end of the hub. A loop tip wire guide is generally not designed to work with the conventional hub provided on the catheter. The loop portion deforms when the loop is advanced into the hub in such a way that the loop is not properly compressed at the loop portion so that the tip of the loop is narrowed for advancement into the narrower lumen of the catheter. Insertion of the loop tip wire guide into a conventional hub may deform the loop so that the loop widens and resists insertion in to the narrower lumen of the catheter.

What is needed is a hub for the reception of a wire guide that is suitable for receiving a conventional wire guide and a loop tip wire guide so that the wire guide is advanceable into the lumen of the catheter.

BRIEF SUMMARY

The various preferred embodiments provide improvements and advantages over conventional hubs configured for receiving straight wire guide tips.

According to one aspect of the present invention, a hub device for reception of a flexible elongate device therethrough is provided. The hub device includes a proximal portion having a substantially cylindrical opening defined in the proximal portion, a first connector at a proximal end of the proximal portion for connecting to a medical device and a distal portion connectable to an elongate shaft. The hub device further includes a lumen extending from the cylindrical opening in the proximal portion to a non-cylindrical cross-sectional lumen portion in the distal portion of the hub device, the lumen including a distal tapered portion tapering to the non-cylindrical cross-sectional lumen portion. The distal tapered portion includes a first pair of longitudinal loop guides positioned on opposite sides of the lumen and configured to receive and collapse a loop of an elongate device received and distally advanced through the lumen.

According to another aspect of the present invention, a medical device for reception of a flexible elongate device therethrough is provided. The medical device includes an elongate shaft and a hub device connected to a proximal portion of the elongate shaft. The hub device includes a proximal portion and a distal portion; and a lumen extending from the proximal portion to the distal portion. The lumen includes a non-cylindrical cross-sectional lumen portion in the distal portion, a distal tapered portion tapering to the non-cylindrical cross-sectional lumen portion, and a first pair of longitudinal loop guides defined in the distal tapered portion and positioned on opposite sides of the lumen and configured to receive and collapse a loop of an elongate device received and distally advanced through the lumen and into a lumen of the elongate shaft.

According to another aspect of the invention, a method of advancing a flexible elongate device through a hub device and into an elongate shaft is provided. The method includes inserting a loop tip of a flexible elongate device into a hub device. The hub device includes a proximal portion having a substantially cylindrical opening defined in the proximal portion and a distal portion connected to an elongate shaft. The hub device further includes a lumen extending from the cylindrical opening in the proximal portion to a non-cylindrical cross-sectional lumen portion in the distal portion, the lumen having a distal tapered portion tapering to the non-cylindrical cross-sectional lumen portion and the distal tapered portion comprising a first pair of longitudinal loop guides positioned on opposite sides of the lumen. The method further includes distally advancing the loop tip from the cylindrical opening to a distal tapered portion, engaging loop portions of the loop tip with the first pair of longitudinal loop guides to orient the loop, and compressing the loop against the first pair of loop guides as the loop advances distally to the non-cylindrical cross-sectional portion and into a lumen of the elongate shaft.

The foregoing paragraphs have been provided by way of general introduction, and are not intended to limit the scope of the following claims. The presently preferred embodiments, together with further advantages will be best understood by reference to the following detailed description taken in conjunction with the accompanying drawings.

BRIEF DESCRIPTION OF THE DRAWINGS

Embodiments of the present invention will now be described by way of example with reference to the accompanying drawings, in which.

DETAILED DESCRIPTION OF THE INVENTION

Figure 1:
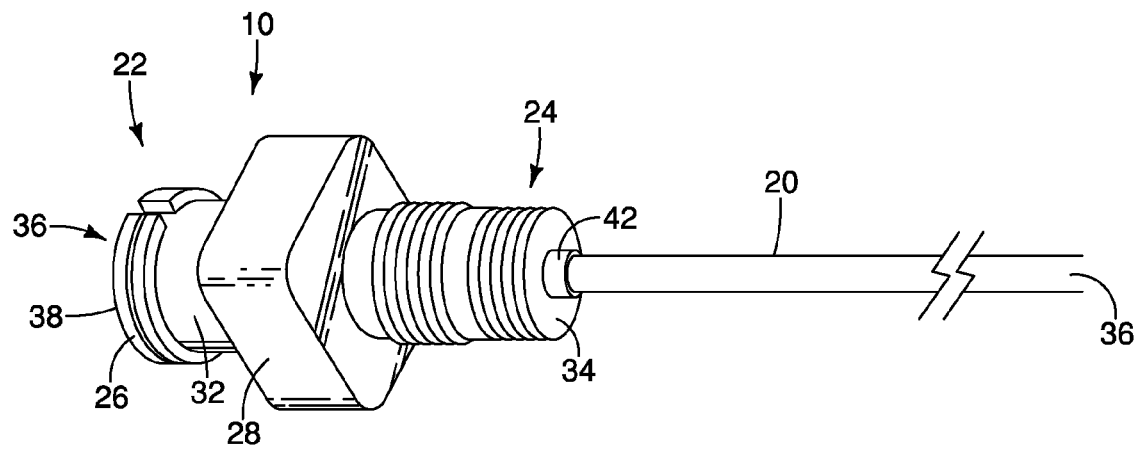
FIG. 1 is a partial perspective view of a wire guide hub connected to a catheter according to an embodiment of the present invention.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

As used in the specification, the terms proximal and distal should be understood as being in the terms of a physician using the wire guide in the hub device. Hence the term distal means the portion of the wire guide hub which is farthest from the physician and the term proximal means the portion of the wire guide hub which is nearest to the physician.

FIG. 1 illustrates a perspective view of a hub 10 according to an embodiment of the invention. The hub 10 is shown connected to a catheter 20, however, the hub 10 may be connected to any type of device through which a wire guide may be inserted. The hub 10 may be removably or non-removably connected to the catheter 20. The hub 10 includes a proximal portion 22 and a distal portion 24. The proximal portion 22 of the hub 10 may include a connector 26. The connector 26 may comprise a thread, flange, protrusion or rib for removably interlocking with a syringe (not shown). By way of non-limiting example, the connector 26 may be a luer connector. The hub 10 may further include a gripping portion 28 that facilitates operation, handling, manipulation and/or movement of the hub 10 by the physician. The gripping portion 28 may have any shape to provide a gripping surface, for example square, hexagonal, or textured and the like. In some embodiments, a setoff 32 may be included distal to the connector 26 and proximal to the gripping portion 28 to facilitate connection of the syringe or other device to the connector 26 without interference with the gripping portion 28. A second connector 34 may be provided at the distal portion 24 of the hub 10 for connecting the hub 10 to an outer catheter or other device (not shown). The second connector 34 may comprise a thread, flange, protrusion or rib for removably interlocking with the second device.

Figure 2:
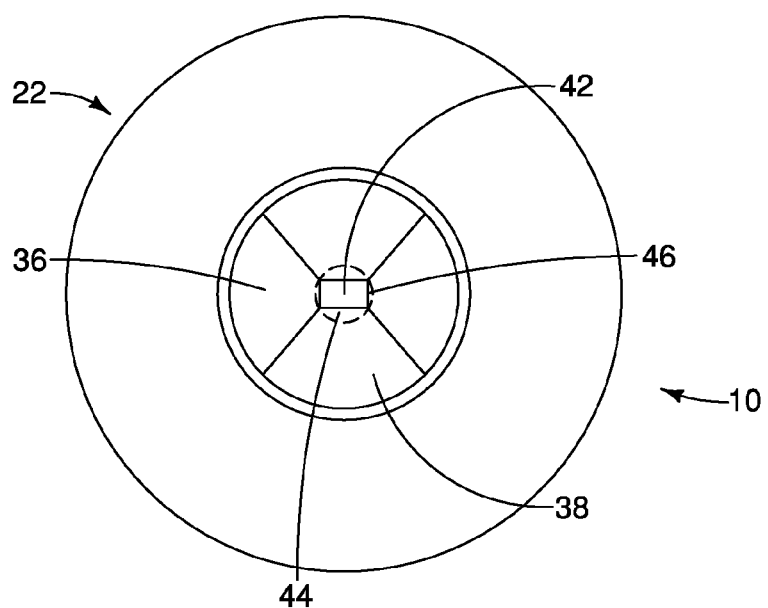
FIG. 2 is an end view of an embodiment of the hub shown in FIG. 1.
Figure 3:
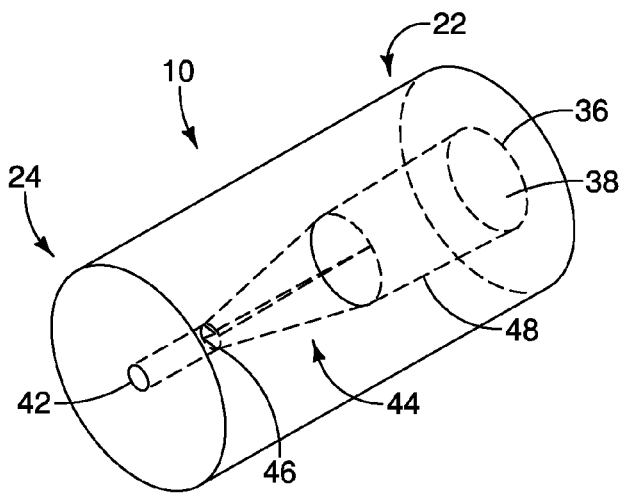
FIG. 3 is a perspective view of the interior of the hub shown in FIG. 2.

A lumen 36 extends through the hub 10 from a proximal opening 38 to a distal opening 42 of the hub 10 and fluidly connects with the catheter 20. An end view from the proximal portion 22 of the hub 10 is shown in FIG. 2. FIGS. 2-5 are schematic drawings where the exterior features are not shown to improve clarity of the interior features depicted in these drawings. The proximal opening 38 tapers to the narrower distal opening 42. As shown in FIGS. 2 and 3, the proximal opening 38 is circular and the lumen narrows through a distal tapered portion 44 to a lumen portion 46 having a non-circular cross sectional shape and to the distal opening 42. FIG. 3 illustrates the features of the interior of the hub 10 and omits the exterior features for clarity. The proximal opening 38 may be sized and shaped according to the conventional luer connection and connected to a proximal lumen portion 48 sized and shaped to receive a syringe or other connection. As shown in FIG. 3, the proximal lumen portion 48 may have a slight taper from the proximal opening 38 to the distal tapered portion 44 and have a generally circular cross sectional shape. The lumen 36 between the proximal opening 38 and the distal opening 42 is generally smooth so that a tip of the wire guide will pass through the lumen 36 without catching at any of the transitions from the proximal opening 38 to the proximal lumen portion 48, the distal tapered portion 44, the lumen portion 46 and the distal opening 42.

Figure 4:
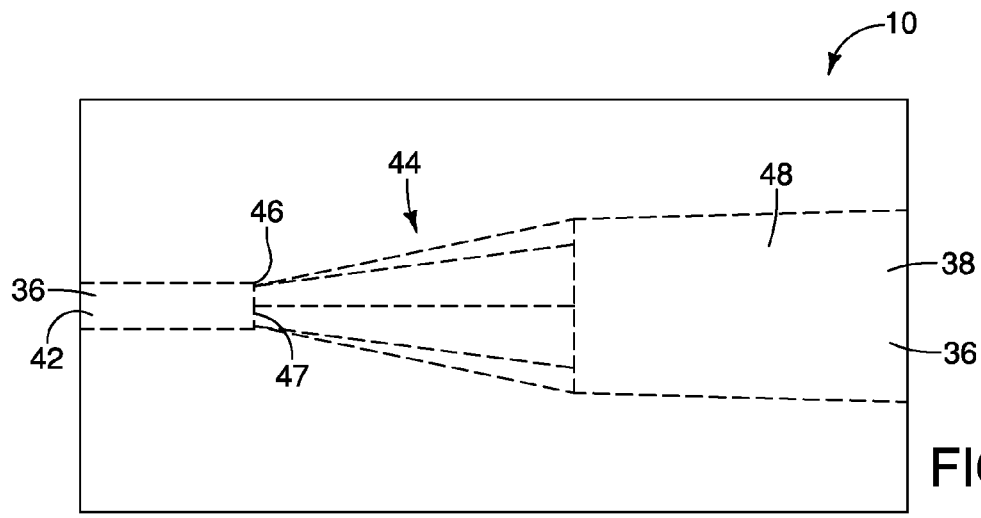
FIG. 4 is a side view of the hub shown in FIG. 3.
Figure 5:
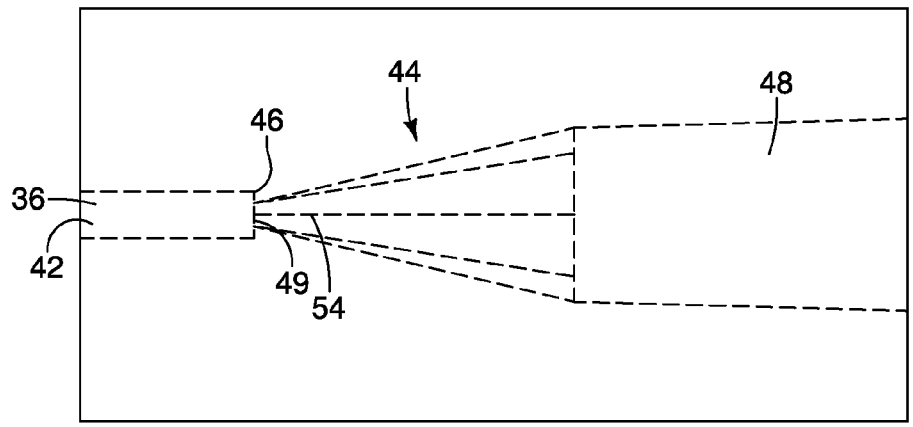
FIG. 5 is a side view of the hub shown in FIG. 4 rotated 90° C.
Figure 7:
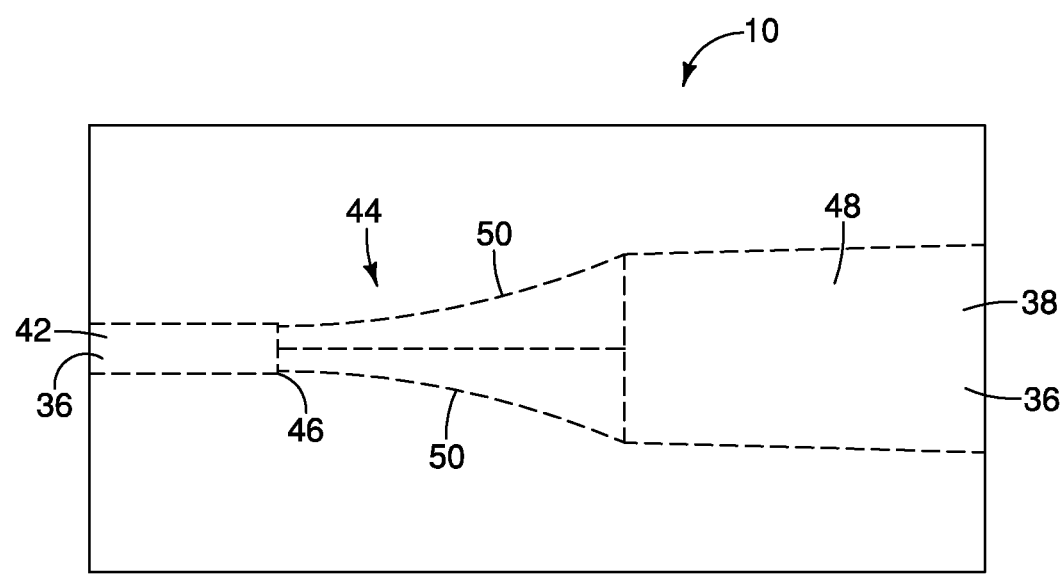
FIG. 7 is a side view of an alternative embodiment of a wire guide hub.

FIGS. 2-5 illustrate the distal tapered portion tapering to a rectangular cross-sectional shape at the lumen portion 46. FIG. 4 shows a side view of the interior features of the hub 10 with the distal tapered portion 44 tapering to a rectangular cross-sectional shape at the lumen portion 46 with a long side 47 of the rectangular lumen portion 46 is shown. FIG. 5 shows a side view of the interior features of the hub 10 that has been rotated 90° from the view shown in FIG. 4 so that a short side 49 of the rectangular lumen portion 46 is shown. As shown in FIG. 7, the lumen 36 may also have walls 50 that bow inward in the distal tapered portion 44. The inward curve of the walls 50 may facilitate orientation and collapse of the loop tip of the wire guide within the hub to narrow and position the tip of the wire guide for insertion into the catheter. (The wire guide is shown in FIGS. 8A-8D and 9A-9C.)

Figure 6A:
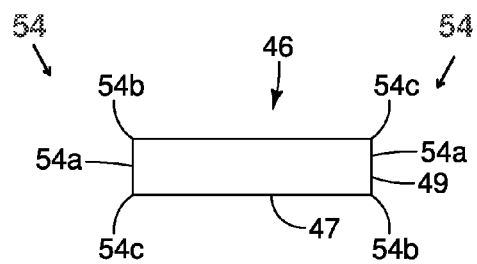
FIGS. 6A-6F illustrate cross-sectional views through the lumen portion of the hub 10.

FIGS. 6A-6F illustrate exemplary non-circular cross sectional shapes of the lumen portion 46. Each of the cross-sectional shapes shown in FIGS. 6A-6F includes at least one pair of loop guides 54 that are configured to engage the sides of the loop of the wire guide to compress and orient the loop for insertion of the tip of the loop into the catheter 20. The loop guides 54 are formed in the distal tapered portion 44 and longitudinally extend along the distal tapered portion 44. The pair of loop guides 54 are positioned on opposite sides of the lumen 36 for reception of the loop. The distal tapered portion 44 narrows to the lumen portion 46 to facilitate the narrowing of the distal tip of the wire guide. The lumen portion 46 may include more than one pair of loop guides, for example, as shown in FIGS. 6A, and 6C-6F. As shown in FIG. 6A, the lumen portion 46 may have a generally rectangular cross-sectional shape that includes a first pair of loop guides 54a formed by the short side walls 49 of the rectangle positioned on opposite sides of the lumen 36. The lumen portion 46 having a rectangular cross-sectional shape may also include a second pair and a third pair of loop guides 54b, 54c formed at the intersection of the short and long side walls 47, 49 of the rectangle. The pairs of loop guides 54b, 54c are preferably are sized to receive the loop of the guide wire without catching or otherwise restricting advancement of the wire guide through the lumen portion 46. In some embodiments, the intersection of the short and long side walls 47, 49 of the rectangle may be curvilinear, for example, rounded, to facilitate advancement of the loop tip. (See FIG. 6A, 54b.)

Figure 6B:
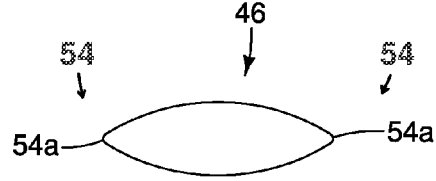
Figure 6C:
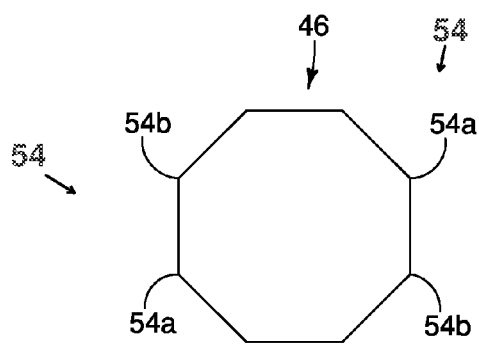
Figure 6D:
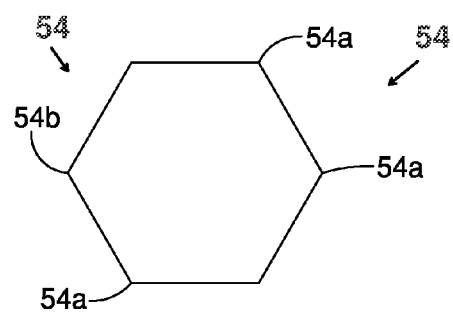
Figure 6E:
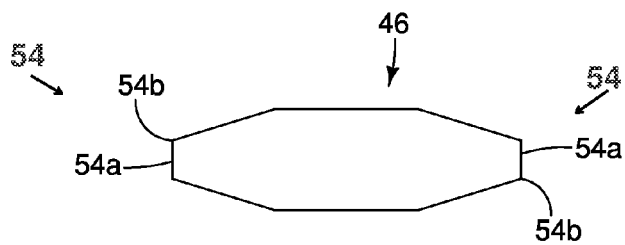
Figure 6F:
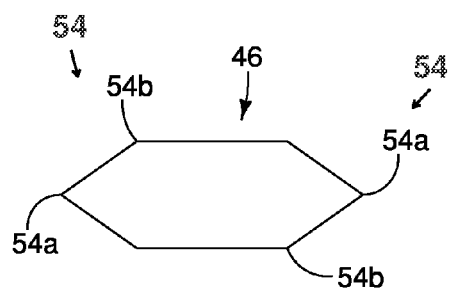

FIG. 6B illustrates a lumen portion 46 having a generally oval cross-sectional shape including a pair of loop guides 54. The loop guides 54 sized and shaped to receive the loop of the guide wire without catching or otherwise restricting advancement of the wire guide through the lumen portion 46. FIGS. 6C and 6D illustrate additional cross-sectional shapes for the lumen portion 46 of the hub 10. FIGS. 6C and 6D show a plurality of pairs of loop guides 54 that are substantially uniformly sized and shaped. The loop tip of the wire guide may be narrowed and advanced using any of the pairs of loop guides 54. In some embodiments, for example as shown in FIGS. 6E and 6F, one of the pairs of loop guides 54 may be more readily configured for reception of the loop tip of the wire guide for orientation and narrowing of the wire guide tip. As shown in FIGS. 6E and 6F, the pair of loop guides 54a is configured to receive the loop tip, although it is possible for the pair of guides 54b to also receive the loop tip. Other non-circular shapes may also be used and the cross-section shapes shown in FIGS. 6A to 6F and provided as non-limiting examples.

Figure 8A:
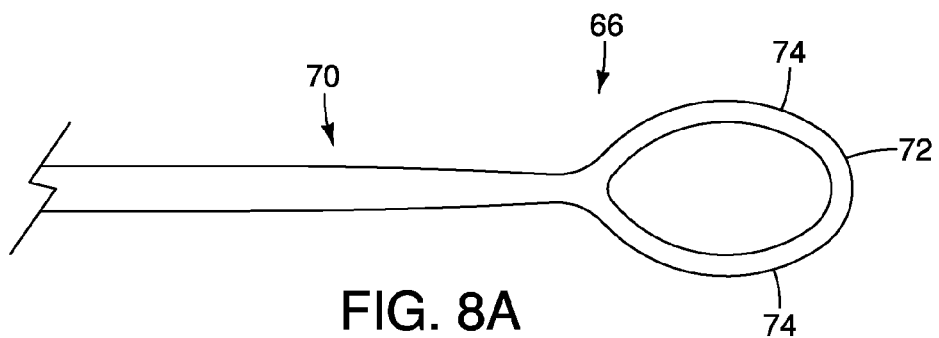
FIGS. 8A-8D illustrate distal portions of wire guides.
Figure 8B:
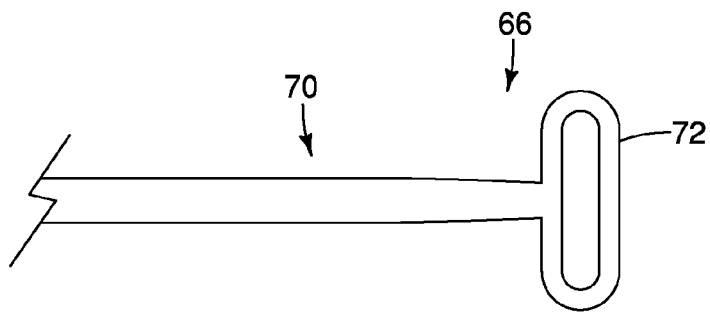
Figure 8C:
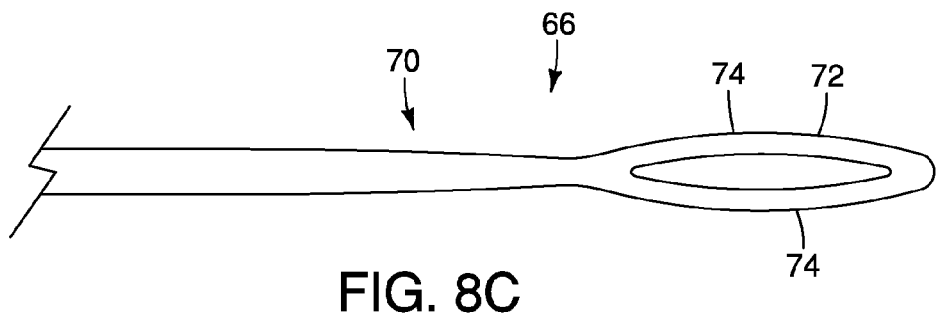
Figure 8D:
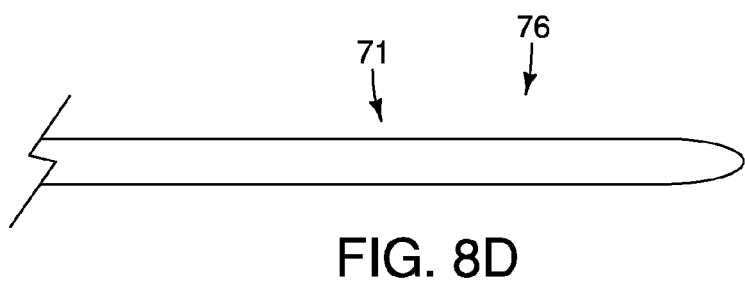

FIGS. 8A-8C illustrate distal portions 66 of wire guides 70. FIG. 8A illustrates the shape of a loop tip 72 of the wire guide 70 prior to insertion of the loop tip 72 into the hub 10. FIG. 8A shows loop portions 74 that contact and are collapsed inward by the pair of loop guides 54 formed in the distal tapered portion 44 of the hub 10. FIG. 8B illustrates the misshapen loop tip 72 of the wire guide 70 that may occur using a conventional hub to connect to the catheter for insertion of the loop tip 72 through the conventional hub and into the catheter. FIG. 8C illustrates the shape of the narrowed and oriented loop tip 72 of the wire guide 70 that has been inserted into the hub 10. FIG. 8D illustrates a conventional wire guide 71 having a straight distal tip 76 that may also be inserted into the hub 10.

Figure 9A:
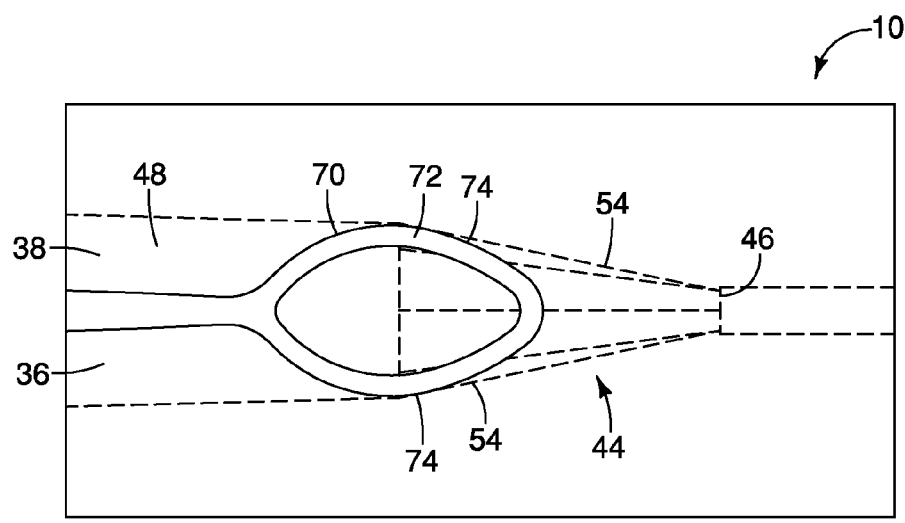
FIGS. 9A-9C illustrate a wire guide being inserted, oriented and narrowed by the hub in accordance with the present invention.
Figure 9B:
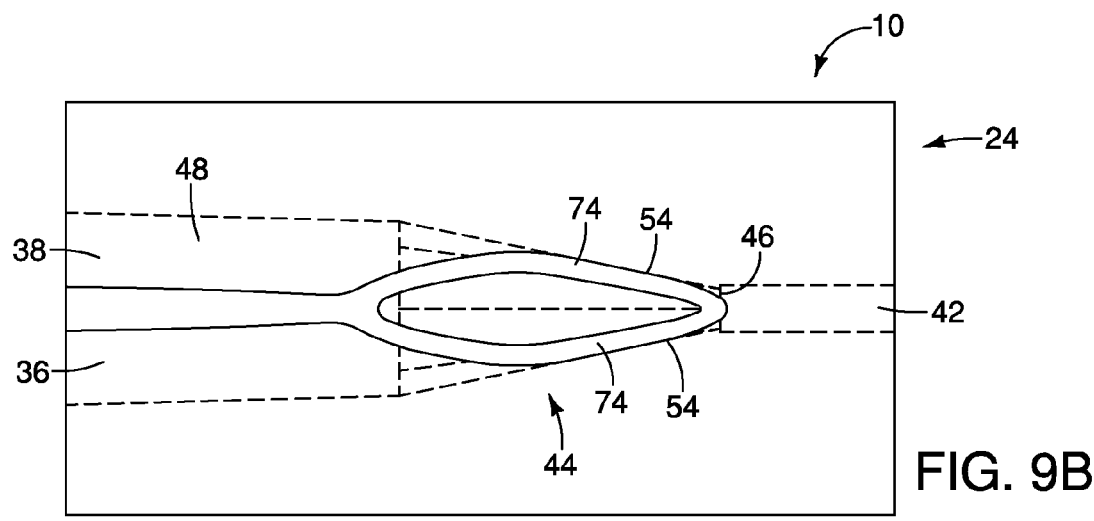
Figure 9C:
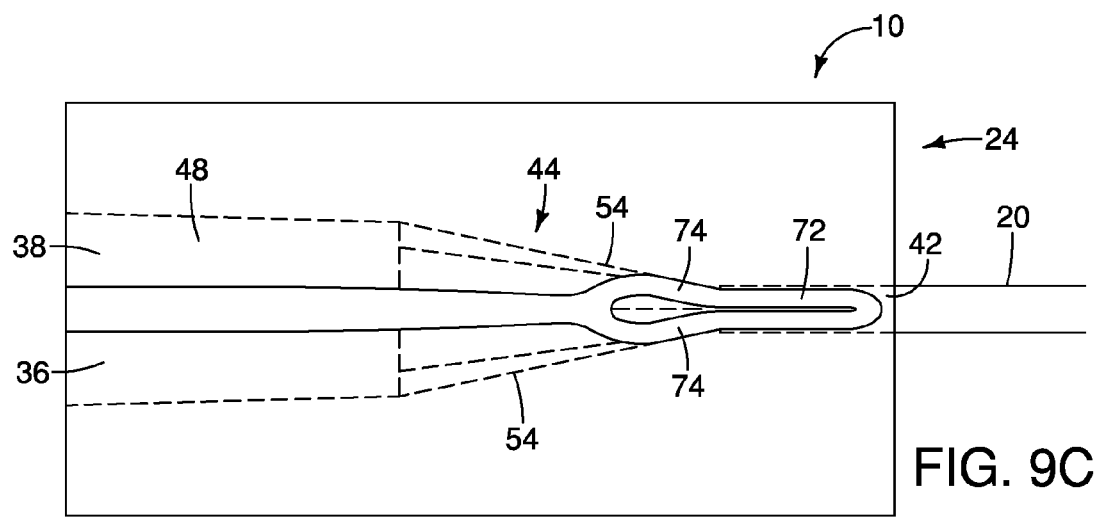

FIGS. 9A-9C illustrate advancement, orientation and narrowing of the loop tip 72 of the wire guide 70 being inserted into the hub 10. FIG. 9A illustrates the loop tip 72 of the wire guide 70 inserted into the lumen 36 of the hub 10 at the proximal opening 38. The loop portions 74 of the loop tip 72 are advanced distally into the distal tapered portion 44 of the hub 10. As the loop tip 72 is distally advanced into the distal tapered portion, the pair of loop guides 54 on opposite sides of the lumen 36 engage and collapse the loop portions 74. FIGS. 9B and 9C illustrate further distal advancement of the loop tip 72 toward the distal portion 24 of the hub 10 so that the loop tip 72 is oriented and collapsed to exit the distal opening 42 and insert into the catheter 20.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. Unless otherwise indicated, all ordinary words and terms used herein shall take their customary meaning as defined in *The New Shorter Oxford English Dictionary*, 1993 *edition*. All technical terms shall take on their customary meaning as established by the appropriate technical discipline utilized by those normally skilled in that particular art area. All medical terms shall take their meaning as defined by *Stedman's Medical Dictionary*, 27*th edition*.

It is therefore intended that the foregoing detailed description be regarded as illustrative rather than limiting, and that it be understood that it is the following claims, including all equivalents, that are intended to define the spirit and scope of this invention.

The invention claimed is:

1. A hub device for reception of a flexible elongate device therethrough, the hub device comprising:
   a proximal portion having a substantially cylindrical opening defined in the proximal portion and a first connector at a proximal end of the proximal portion for connecting to a medical device;
   a distal portion adapted to be connected to an elongate shaft; and
   a lumen extending from the cylindrical opening in the proximal portion to a non-cylindrical cross-sectional lumen portion in the distal portion, the lumen having a distal tapered portion tapering to the non-cylindrical cross-sectional lumen portion, the distal tapered portion comprising a first pair of longitudinal loop guides positioned on opposite sides within the lumen and configured to receive and collapse a loop of an elongate device received and distally advanced through the lumen.

2. The hub device of claim 1, wherein the non-cylindrical cross-sectional lumen portion comprises a substantially polygonal shape.

3. The hub device of claim 2, wherein the non-cylindrical cross-sectional lumen portion comprises a substantially rectangular shape.

4. The hub device of claim 1, wherein the non-cylindrical cross-sectional lumen portion comprises a substantially oval shape.

5. The hub device of claim 1, wherein the first connector is a luer connector.

6. The hub device of claim 1, wherein the distal portion comprises a second connector.

7. The hub device of claim 1, wherein the distal tapered portion comprises a second pair of longitudinal loop guides within the distal tapered portion.

8. The hub device of claim 1, wherein a first and second intersection of lumen walls forming the first pair of longitudinal loop guides are curvilinear to facilitate advancement of the loop.

9. The hub device of claim 1, wherein the proximal portion comprises a lumen taper.

10. The hub device of claim 1, wherein the distal portion is adapted to be non-removably connected to an elongate shaft.

11. The hub device of claim 1, wherein the hub device further comprises a gripping portion.

* * * * *